US010953215B2

(12) United States Patent
Adams et al.

(10) Patent No.: US 10,953,215 B2
(45) Date of Patent: Mar. 23, 2021

(54) NON-LUER COMPATIBLE ADMINISTRATION PORT

(71) Applicant: Dale Medical Products, Inc., Plainville, MA (US)

(72) Inventors: David Preston Adams, North Hampton, NH (US); Alan Kenneth Stratton, Milford, NH (US); Joseph A. Zilaro, Sturbridge, MA (US); Sharon Steeves, Bellingham, MA (US); Raymond Gruneberg, Warwick, RI (US)

(73) Assignee: DALE MEDICAL PRODUCTS, INC., Plainville, MA (US)

( * ) Notice: Subject to any disclaimer, the term of this patent is extended or adjusted under 35 U.S.C. 154(b) by 413 days.

(21) Appl. No.: 15/094,880

(22) Filed: Apr. 8, 2016

(65) Prior Publication Data

US 2016/0296740 A1  Oct. 13, 2016

Related U.S. Application Data

(60) Provisional application No. 62/144,752, filed on Apr. 8, 2015.

(51) Int. Cl.
*A61M 39/10* (2006.01)
*A61M 39/00* (2006.01)
*A61M 39/24* (2006.01)

(52) U.S. Cl.
CPC ..... *A61M 39/10* (2013.01); *A61M 2039/0072* (2013.01); *A61M 2039/1072* (2013.01);
(Continued)

(58) Field of Classification Search
CPC .. A61M 2039/2473; A61M 2039/0072; A61M 39/10; A61M 2039/1072;
(Continued)

(56) References Cited

U.S. PATENT DOCUMENTS 3,610,228 A * 10/1971 Temkin .............. A61B 5/02156
  600/486
3,721,265 A * 3/1973 Hoffland ................. F16K 11/08
  137/625.47
(Continued)

FOREIGN PATENT DOCUMENTS

WO   WO/2014/095351   *  6/2014

OTHER PUBLICATIONS

International Organization for Standardization, International Standard ISO 594/1-1986(E), "Conical fittings with a 6% (Luer) taper for syringes, needles and certain other medical equipment—Part 1: General requirements" First Edition. Switzerland: ISO, Jun. 15, 1986; 12 pages.
(Continued)

*Primary Examiner* — Bhisma Mehta
*Assistant Examiner* — James D Ponton
(74) *Attorney, Agent, or Firm* — Burns & Levinson LLP (57) ABSTRACT

The present disclosure provides a medical connector for enteral applications. The medical connector includes a body portion having a distal patient access fitting and a proximal fluid delivery device fitting as well as an administration port. The administration port for administrating or extracting fluids or medicine includes a cylindrical cavity, an administration port seal having a normally-closed slit, a plunger, a plunger sleeve, and a compression member. Engaging a non-luer female tip with the administration port actuates the compression member such that the plunger pierces the normally-closed slit, causing it to open allowing fluid communication with the body portion.

19 Claims, 8 Drawing Sheets

(52) U.S. Cl.
CPC ............ *A61M 2039/1083* (2013.01); *A61M 2039/1088* (2013.01); *A61M 2039/1094* (2013.01); *A61M 2039/2473* (2013.01)

(58) Field of Classification Search
CPC .. A61M 2039/1083; A61M 2039/1088; A61M 2039/1094; A61M 2039/2426
See application file for complete search history.

(56) References Cited

U.S. PATENT DOCUMENTS

| | | | | |
|---|---|---|---|---|
| 3,774,604 A * | 11/1973 | Danielsson | ....... | A61M 39/0606 137/625.47 |
| 3,834,372 A * | 9/1974 | Turney | ................ | A61B 5/0215 137/625.47 |
| 3,952,729 A * | 4/1976 | Libman | ................ | B01L 3/0206 600/575 |
| 4,219,021 A * | 8/1980 | Fink | .................... | A61M 39/223 137/556.6 |
| 4,252,122 A * | 2/1981 | Halvorsen | ............. | A61M 39/10 604/264 |
| 4,447,235 A * | 5/1984 | Clarke | ............... | A61B 17/3415 600/573 |
| 4,819,684 A * | 4/1989 | Zaugg | .................... | A61M 39/02 137/112 |
| 4,915,687 A * | 4/1990 | Sivert | .................... | A61M 39/02 137/605 |
| 4,949,723 A * | 8/1990 | Wallace | ................ | A61B 5/021 600/485 |
| 4,967,797 A * | 11/1990 | Manska | .............. | A61M 39/223 137/625.47 |
| 4,981,140 A * | 1/1991 | Wyatt | .................... | A61B 5/411 600/486 |
| 5,046,528 A * | 9/1991 | Manska | ................ | F16K 31/602 137/385 |
| 5,252,064 A * | 10/1993 | Baum | ................ | A61C 17/0202 433/80 |
| 5,267,983 A | 12/1993 | Oilschlager et al. | | |
| 5,269,771 A * | 12/1993 | Thomas | .............. | A61M 39/045 251/149.1 |
| 5,340,364 A * | 8/1994 | Ghelli | .................... | A61M 1/367 604/30 |
| 5,354,267 A * | 10/1994 | Niermann | ......... | A61M 16/0463 128/207.14 |
| 5,466,228 A * | 11/1995 | Evans | ................. | A61M 39/223 137/625.47 |
| 5,533,549 A * | 7/1996 | Sherman | ............... | F16K 27/067 137/556.6 |
| 5,540,668 A * | 7/1996 | Wilson, Jr. | .......... | A61M 39/223 137/625.41 |
| 5,603,706 A | 2/1997 | Wyatt et al. | | |
| 5,605,630 A * | 2/1997 | Shibata | .................... | A61M 1/16 210/143 |
| 5,618,268 A * | 4/1997 | Raines | .................. | A61M 39/24 604/247 |
| 5,776,117 A | 7/1998 | Haselhorst et al. | | |
| 5,782,816 A * | 7/1998 | Werschmidt | .......... | A61M 39/02 137/903 |
| 6,165,168 A | 12/2000 | Russo | | |
| 6,171,287 B1 * | 1/2001 | Lynn | .................... | A61M 39/02 251/149 |
| 6,177,049 B1 * | 1/2001 | Schnell | ................ | A61M 1/367 422/44 |
| 6,269,704 B1 * | 8/2001 | Ziv | ....................... | A61M 39/02 600/573 |
| 6,418,966 B2 * | 7/2002 | Loo | .................... | A61M 39/223 137/625.47 |
| 6,439,262 B1 * | 8/2002 | Hosono | ................ | F15B 11/028 137/382 |
| 6,457,488 B2 * | 10/2002 | Loo | .................... | A61M 39/223 137/625.47 |
| 6,569,117 B1 * | 5/2003 | Ziv | ....................... | A61M 39/02 604/164.01 |
| 6,626,884 B1 * | 9/2003 | Dillon | .................... | A61M 1/02 600/573 |
| 6,706,022 B1 * | 3/2004 | Leinsing | ............... | A61M 39/26 604/247 |
| 6,834,842 B2 * | 12/2004 | Houde | .............. | A61M 39/0613 251/149.1 |
| 6,855,138 B2 * | 2/2005 | Tsai | ....................... | A61M 39/26 604/537 |
| 7,033,339 B1 * | 4/2006 | Lynn | .................... | A61M 39/02 604/246 |
| 7,081,109 B2 * | 7/2006 | Tighe | .................... | A61M 39/20 604/500 |
| 7,172,572 B2 * | 2/2007 | Diamond | ............. | A61M 39/223 137/625.21 |
| 7,184,825 B2 * | 2/2007 | Leinsing | ............... | A61M 39/26 604/20 |
| 7,223,257 B2 * | 5/2007 | Shubayev | ......... | A61M 39/0247 604/175 |
| 7,510,545 B2 * | 3/2009 | Peppel | ................ | A61M 39/045 604/256 |
| 7,744,573 B2 * | 6/2010 | Gordon | ................ | A61B 5/0215 600/584 |
| 7,771,383 B2 * | 8/2010 | Truitt | .................... | A61M 39/02 604/246 |
| 7,867,204 B2 * | 1/2011 | Bartholomew | ....... | A61M 39/02 251/337 |
| 7,875,020 B2 * | 1/2011 | Tighe | .................... | A61M 39/20 604/539 |
| 7,963,951 B2 * | 6/2011 | Kitani | ................. | A61M 39/223 137/625 |
| 7,984,730 B2 * | 7/2011 | Ziv | ..................... | A61M 39/223 137/239 |
| 7,988,128 B2 * | 8/2011 | Wentling | .............. | A61M 39/10 251/286 |
| 7,993,328 B2 * | 8/2011 | Whitley | ............. | A61M 39/1011 604/537 |
| 8,002,727 B2 * | 8/2011 | Brugger | .............. | A61M 1/3626 137/625.42 |
| 8,221,389 B2 * | 7/2012 | Brenner | ............... | A61J 15/0015 604/248 |
| 8,241,268 B2 * | 8/2012 | Whitley | ............. | A61M 39/1011 604/537 |
| 8,277,424 B2 | 10/2012 | Pan | | |
| 8,298,196 B1 * | 10/2012 | Mansour | ................ | A61M 39/04 604/256 |
| 8,353,895 B2 | 1/2013 | Russo | | |
| 8,435,210 B2 | 5/2013 | Zinger et al. | | |
| 8,534,321 B2 * | 9/2013 | Ziv | ..................... | A61M 39/223 137/239 |
| 8,584,701 B2 * | 11/2013 | Duncan | ................ | F16K 11/0853 137/555 |
| 8,641,012 B2 | 2/2014 | Matsumoto et al. | | |
| 8,715,222 B2 * | 5/2014 | Truitt | .................... | A61M 39/02 604/246 |
| 9,016,316 B2 * | 4/2015 | Ziv | ..................... | A61M 39/223 137/239 |
| 9,192,753 B2 | 11/2015 | Lopez et al. | | |
| 9,212,762 B2 * | 12/2015 | Duncan | ................ | F16K 11/0853 |
| 9,234,616 B2 | 1/2016 | Carrez et al. | | |
| 9,375,561 B2 * | 6/2016 | Mansour | ............. | A61M 39/223 |
| 9,500,287 B2 * | 11/2016 | Duncan | ............... | A61M 39/223 |
| 2003/0199835 A1 | 10/2003 | Leinsing | ............... | A61M 39/26 604/256 |
| 2004/0210162 A1 * | 10/2004 | Wyatt | ................ | A61B 5/15003 600/573 |
| 2006/0027270 A1 * | 2/2006 | Truitt | .................... | A61M 39/02 137/843 |
| 2006/0089603 A1 * | 4/2006 | Truitt | .................... | A61M 39/02 604/246 |
| 2006/0266421 A1 * | 11/2006 | Chilvers | .............. | A61M 39/24 137/515 |
| 2007/0112323 A1 * | 5/2007 | Daly | ..................... | A61J 1/1406 604/411 |
| 2007/0219483 A1 * | 9/2007 | Kitani | ................... | A61M 39/10 604/32 |

(56) References Cited

U.S. PATENT DOCUMENTS

| | | | |
|---|---|---|---|
| 2007/0287953 A1* | 12/2007 | Ziv | A61M 39/223 604/31 |
| 2008/0058720 A1* | 3/2008 | Spohn | A61M 5/007 604/140 |
| 2009/0171322 A1* | 7/2009 | Kurimoto | A61M 5/347 604/533 |
| 2009/0182309 A1 | 7/2009 | Muffly | |
| 2010/0004634 A1* | 1/2010 | Whitley | A61M 39/1011 604/537 |
| 2010/0063440 A1* | 3/2010 | Kitani | A61M 39/045 604/83 |
| 2011/0257606 A1* | 10/2011 | Truitt | A61M 39/02 604/246 |
| 2012/0059334 A1* | 3/2012 | Pan | A61M 39/10 604/236 |
| 2012/0103448 A1* | 5/2012 | Hopf | A61M 39/223 137/625 |
| 2012/0130305 A1* | 5/2012 | Bonnal | A61M 39/02 604/30 |
| 2012/0157914 A1 | 6/2012 | Stroup | |
| 2012/0316514 A1* | 12/2012 | Mansour | A61M 39/04 604/256 |
| 2013/0060205 A1* | 3/2013 | Mansour | A61M 39/223 604/248 |
| 2013/0267903 A1 | 10/2013 | Bomgaars | |
| 2014/0014207 A1* | 1/2014 | Ziv | A61M 39/223 137/625.46 |
| 2014/0021714 A1 | 1/2014 | Ueda et al. | |
| 2014/0228778 A1* | 8/2014 | Ma | A61M 39/221 604/256 |
| 2014/0257198 A1* | 9/2014 | Truitt | A61M 39/02 604/246 |
| 2014/0276215 A1* | 9/2014 | Nelson | A61M 39/225 600/573 |
| 2015/0157534 A1* | 6/2015 | Van Puijenbroek | B65D 75/5877 206/525 |
| 2015/0196749 A1* | 7/2015 | Ziv | A61M 39/223 137/625.47 |
| 2015/0196750 A1* | 7/2015 | Ueda | A61M 39/045 251/149.1 |
| 2015/0231309 A1* | 8/2015 | Bihlmaier | A61L 29/16 424/405 |
| 2015/0238747 A1* | 8/2015 | Russo | A61M 39/1011 604/533 |
| 2015/0306370 A1* | 10/2015 | Liu | A61M 39/22 604/256 |
| 2015/0320638 A1* | 11/2015 | Becker | A61J 1/1475 215/306 |

OTHER PUBLICATIONS

International Organization for Standardization, International Standard ISO 594-2:1998(E), "Conical fittings with a 6% (Luer) taper for syringes, needles and certain other medical equipment—Part 2: Lock Fittings" Second Edition. Switzerland: ISO, Sep. 1, 1998; 16 pages.

International Organization for Standardization, Draft International Standard ISO/DIS 80369-3.2, "Small-bore connectors for liquids and gases in healthcare applications—Part 3: Connectors for enteral applications" Switzerland: ISO, Sep. 25, 2014; 48 pages.

* cited by examiner

NON-LUER COMPATIBLE ADMINISTRATION PORT

CROSS-REFERENCE TO RELATED APPLICATION

This application is based upon and claims the benefit of priority of U.S. Provisional Application No. 62/144,752, filed on Apr. 8, 2015, the entirety of which is incorporated herein by reference.

TECHNICAL FILED

The present disclosure relates to medical connector devices for enteral applications.

BACKGROUND

The present disclosure relates to medical connector devices used to link or join medical devices for fluid or gas delivery applications such as enteral feeding sets, catheters, and other medical devices.

Fluid and gas delivery systems are common in medical applications, and utilize various catheters, tubing, and syringes for fluid and/or gas delivery to patients. Intravenous ("I.V.") catheters are typically used to administer I.V. medications into a patient's I.V. or arterial system using catheters having luer fittings defined as set forth in ISO 594:1986 "Conical fittings with a 6% (Luer) taper for syringes, needles and certain other medical equipment" standards ("ISO/ANSI 1986"), which is one type of small-bore connectors. An ISO/ANSI 1986 compliant, or luer catheter typically has a female rigid luer fitting which will fit into a male luer I.V. syringe or I.V. extension or I.V. administration set. From the luer dimensional ISO/ANSI 1986 standards, the luer tip has an outside diameter of 4 mm, a fluid flow path of less than 2.4 mm in diameter, and a length of less than 0.300 inches with a 6% taper. The luer taper is one possible configuration of a small-bore connector common in the healthcare setting. A small-bore connector commonly refers to a connector with an inner diameter of less than 8.5 mm.

Enteral connectors, which are typically small-bore connectors, may take various forms, and recently, at least one worldwide organization seeks to standardize enteral connectors to have non-luer compatible forms, such that misconnections of wrong systems (e.g., administering/connecting I.V. fluids into an enteral system or vice-versa) are reduced or prevented. Previous connector designs have allowed luer tip or luer lock syringes to connect to an enteral catheter. As the administration of enteral formula into a patient's I.V. system can have catastrophic effects leading to serious complications and/or death, a mechanical solution that prevents such misconnections is desirable.

Recently, standards have been proposed for non-luer compatible fittings of all syringes, feeding tubes, and delivery sets having small bore connector fittings with less than 8.5 mm in diameter fluid flow path for enteral administration. These standards have been issued as proposed ISO/ANSI 80369-3 "Small-bore connectors for liquids and gases in healthcare applications—part 3: connectors for enteral applications" standards and set forth in AAMI/CN3:2014 (hereinafter, "AAMI/CN3:2014 and ISO/ANSI 80369-3"). The standards delineate certain requirements for syringes, feeding tubes, and delivery sets having totally non-luer compatible male and female screw-thread type fittings. One such proposed AAMI/CN3:2014 and ISO/ANSI 80369-3 standard connector is presently referred to as the ENFit connector, and has the screw-thread type fitting described in the standard. Connectors that accommodate the screw-thread type fittings and that prevent connection with luer fittings are desirable.

SUMMARY

Medical connectors, such as the present Dale ACE Connector®, may have a proximal fluid delivery port, and a distal patient access port. Some connectors, such as the present Dale ACE Connector®, include a third port, which operates as a medicine, flush, residual gastric, and/or administration port, through which clinicians can administer medications or other fluids, or sample fluids, without having to disconnect the delivery system utilizing the connector. The administration port may be referred to as a syringe port, although other devices may insert into the port. The administration port may be used to administer fluid flushes, medication with fluid, enteral formula, or for sampling gastric residuals, for example.

Advantageously, the present Dale ACE Connector® provides a closed-to-atmosphere seal and a normally closed off to atmosphere fluid controller, preventing any potentially infectious enteral stomach contents from exiting out either the seal or proximal fluid delivery port. The inventors have recognized that an administration port configuration that is non-luer compatible, provides a closed-to-atmosphere seal, and functions with a screw-thread type fitting, would be advantageous in a connector device. The inventors have also recognized that an administration port configuration that may reduce and prevent obstruction during dispensing, administration, sampling, and/or withdrawal of various of types of fluids would be advantageous in enteral applications. Using the inventive connector, a clinician may administer or dispense a variety of fluids, such as water, saline, crushed slurry of medications, liquid medications, commercial enteral formulas, home-blended enteral formulas, and more viscous (e.g., thicker or coarser) enteral formulas or blended formulas through the inventive connector. Medication slurries and enteral formulas, for example, vary in smoothness, viscosity, and uniformity depending on how they are crushed or blended before being dispensed through an administration port, such as an ENFit syringe. Such dispensing would typically be performed in combination with appropriate size enteral feeding tubes, such as Salem or Levin tubes, Kangaroo or Dobbhoff tubes.

In one embodiment of the present disclosure, a medical connector for enteral applications may include a body portion having a distal patient access fitting, a proximal fluid delivery device fitting, and an administration port. The administration port may include a first cylindrical cavity, an administration port seal having a normally-closed slit, a plunger, a plunger sleeve, and a compression member. Engaging a non-luer female tip with the administration port actuates the compression member such that the plunger pierces the normally-closed slit, whereby the normally-closed slit opens. The distal patient access fitting, the proximal fluid delivery device fitting, and the administration port may all be in fluid communication with a fluid flow path positioned within the body portion.

In some embodiments, the female tip may include at least one threaded sector, and the cylindrical cavity may include a complementary threaded sector such that the female tip may engage with the administration port using a rotational movement, causing the threaded sector to traverse the complementary threaded sector. The female tip and cylindrical cavity preferably have dimensions in compliance with those dimensions set forth in AAMI/CN3:2014 and ISO/ANSI 80369-3.

In yet another embodiment, the plunger of the medical connector may include a second cylindrical cavity and may have an external ring disposed outside the second cylindrical cavity. The external ring is disposed about the compression member such that a downward force on the plunger, the external ring, and/or the second cylindrical cavity actuates the compression member. The second cylindrical cavity may have an elongated tapered shape extending throughout the inside of the plunger and has an internal diameter nominally of 2.9 mm at a first end and an internal diameter nominally of 3.9 mm at a second end.

In some embodiments, the plunger may include a top portion, e.g., above the ring and a bottom portion, e.g., below the ring, wherein the top portion is made of a material softer than the bottom portion. In one embodiment, the ring may be made of the same material as the top portion. In another embodiment, the top portion may be made of santoprene. In yet another embodiment, the bottom portion may be made of high-density polyethylene (HDPE) or high-density polypropylene (HDPP). In other embodiments, the top portion, the ring, and/or the bottom portion may be made of a blended formulation comprising high-density polyethylene (HDPE) or high-density polypropylene (HDPP) and santoprene. The proportion of the HDPE or HDPP in the blended formulation may range from about 5 to about 15%. In some embodiments, the top portion and/or the ring may include a chamfered edge.

A medical connector consistent with the present disclosure may also have a normally biased closed-to-atmosphere seal and a fluid flow controller disposed between the seal and the proximal fluid delivery device fitting. The fluid flow controller may be a manually operated turn handle. Such a turn handle may have fixed stop positions for both an on and off fluid flow positions. When the turn handle is at the on fluid flow position, the distal patient access fitting, the proximal fluid delivery device fitting, and the administration port may all be in fluid communication with a fluid flow path positioned within the body portion.

In still other embodiments, the proximal fluid delivery device fitting may be permanently or temporarily attached to an enteral feeding administration set, or to the tubing thereof. The medical connector may be permanently or temporarily attached mid-tube of an enteral feeding administration set. Generally, the disclosed embodiments may be used with enteral feeding tubing, Patient Feeding Tube-Adult, pediatric or neonatal, Balloon Replacement Tube—(BRT), Salem Sump Tube, Levin Tube, PEG Tube (percutaneous endoscopic gastronomy tube), PEJ Tube, G-J Tube, or other suitable tubing or administration set.

Also consistent with the present disclosure, the distal patient access fitting, the proximal fluid delivery device fitting, and/or body portion may have a fluid flow path whose internal diameter is nominally 2.9 mm.

Additional objects and advantages of the present disclosure will be set forth in part in the description which follows, and in part will be obvious from the description, or may be learned by practice of the present disclosure. The objects and advantages of the present disclosure will be realized and attained by means of the elements and combinations particularly pointed out in the appended claims.

It is to be understood that both the foregoing general description and the following detailed description are exemplary and explanatory only and are not restrictive of the invention, as claimed. The present disclosure is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be used as a basis for designing other structures, devices, and systems for carrying out the several purposes of the present disclosure. It is important, therefore, to recognize that the claims should be regarded as including such equivalent constructions insofar as they do not depart from the spirit and scope of the present disclosure.

BRIEF DESCRIPTION OF THE DRAWINGS

The accompanying drawings, which are incorporated in and constitute a part of this specification, illustrate embodiments of the present disclosure and, together with the description, explain the principles of the disclosure.

DETAILED DESCRIPTION

Reference will now be made in detail to the exemplary embodiments of the present disclosure described below and illustrated in the accompanying drawings. Wherever possible, the same reference numbers will be used throughout the drawings to refer to the same or like parts.

While the present disclosure is described herein with reference to illustrative embodiments of particular applications, such as medical connector devices and systems for enteral applications, it is understood that the embodiments described herein are not limited thereto. Those having ordinary skill in the art and access to the teachings provided herein will recognize additional modifications, applications, embodiments, and substitution of equivalents that all fall within the scope of the present disclosure.

Figure 1A:
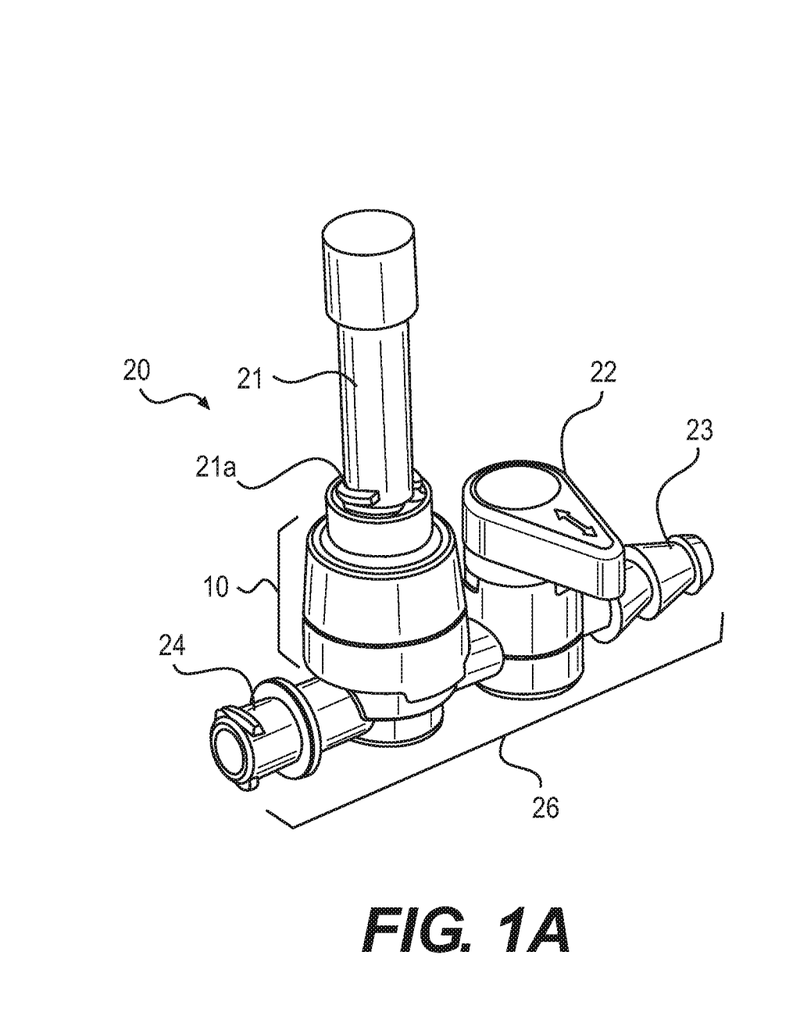
FIG. 1A shows a perspective view of an exemplary medical connector consistent with the present disclosure.
Figure 1B:
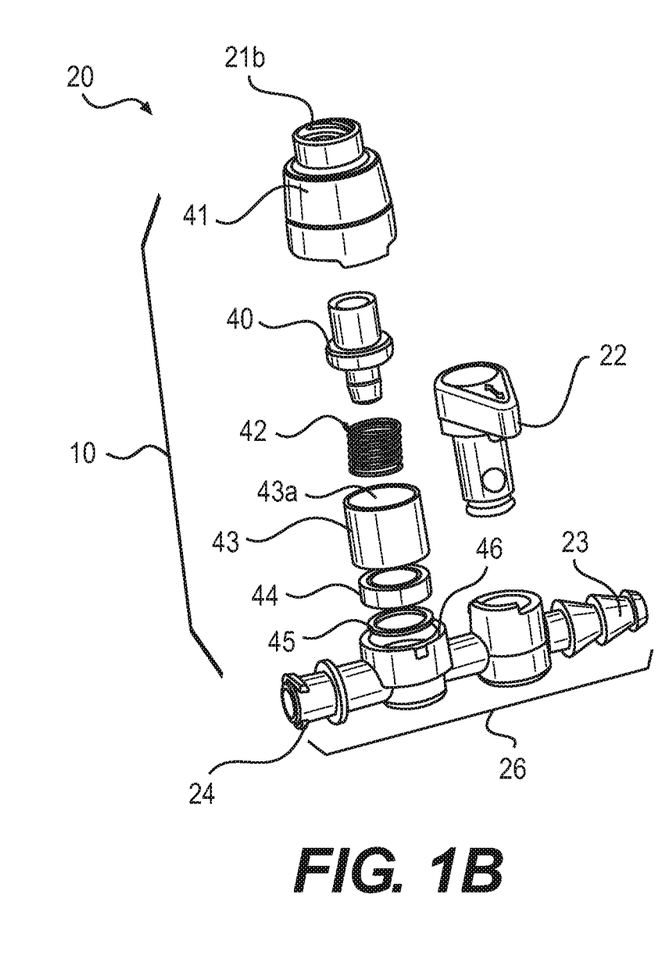
FIG. 1B shows a component view of the exemplary medical connector of FIG. 1A consistent with the present disclosure.

FIG. 1A shows a perspective view of an exemplary medical connector 20 and FIG. 1B shows a component view of medical connector 20 consistent with the present disclosure. As shown in FIGS. 1A and 1B, medical connector 20 is a three port connector that includes a first port including a distal patient access fitting 24, a second port including a proximal fluid delivery device fitting 23, and a third administration port 10 that may receive a syringe fitting 21 of a suitable syringe. For example, syringe fitting 21 is shown as being inserted into administration port 10. Syringe fitting 21 may include a threaded sector 21a and administration port 10 may include a complementary threaded sector 21b. Syringe fitting 21 may be inserted by using a rotational movement causing threaded sector 21a to traverse complementary threaded sector 21b inside administration port 10 in compliance with AAMI/CN3:2014 and ISO/ANSI 80369-3, or other applicable standards.

Figure 5A:
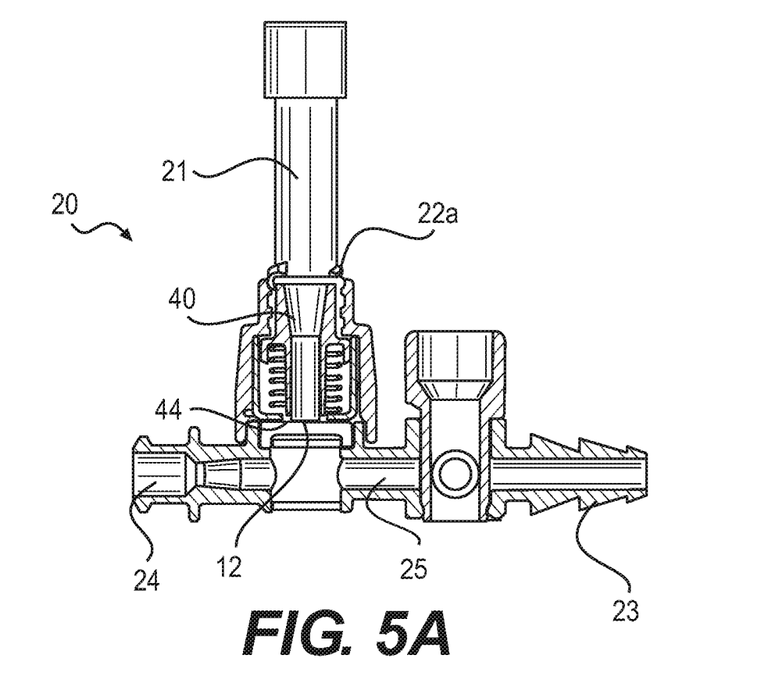
FIG. 5A shows a cross-sectional view of the exemplary medical connector of FIGS. 1A-2C with an exemplary syringe ready to actuate the exemplary plunger, and the exemplary administration port slit is closed.
Figure 5B:
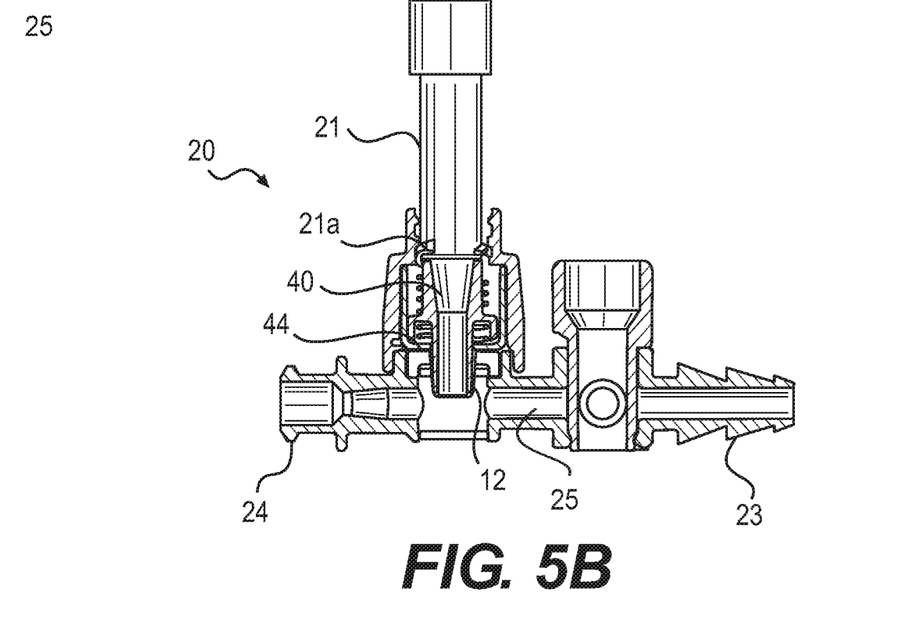
FIG. 5B shows another cross-sectional view of the exemplary medical connector of FIGS. 1A-2C with the exemplary syringe actuating the plunger, causing the administration port slit to open.

As shown in FIGS. 1A and 1B, medical connector 20 further includes a body portion 26 that includes the proximal fluid delivery device fitting 23 and the distal patient access fitting 24. Medical connector 20 may further include a fluid controller 22. Fluid controller 22 may be a manually-operated turn handle, and may have fixed stop positions for both the on and off fluid flow positions. When fluid controller 22 is in the off position, fluid communication from proximal fluid delivery device fitting 23 to distal patient access fitting 24 is prevented by blocking the fluid flow path 25 (as shown in FIGS. 5A and 5B) from proximal fluid delivery device fitting 23 to distal patient access fitting 24 within the body portion 26. In some embodiments, distal patient access fitting 24 has a fluid flow path whose internal diameter is nominally 2.9 mm, and further, proximal fluid delivery device fitting 23 may also have a fluid flow path whose internal diameter is nominally 2.9 mm.

Medical connector 20 may further include a plunger 40, a valve cap 41, with which syringe fitting 21 engages, a compression member 42 (e.g., a spring), a plunger sleeve 43, an administration port valve 44, a washer 45, and/or a base 46. Plunger 40, valve cap 41, compression member 42, plunger sleeve 43, administration port valve 44, and/or washer 45, may be disposed within administration port 10, and be part of administration port 10. As shown in FIG. 1B, along body portion 26 of medical connector 20 is base 46, which removably or fixedly attaches to administration port 10. Administration port valve 44 may be contained in base 46, as described herein. While the components are shown separately in FIG. 1B, many of the components may be combined and manufactured as one component or permanently fused to one or more of the other components.

Valve cap 41 has complementary threaded sector 21b. For example, complementary threaded sector 21b could accommodate a syringe tip in compliance with AAMI/CN3:2014 and ISO/ANSI 80369-3. Valve cap 41 and/or plunger sleeve 43 may be part of administration port 10, and together, valve cap 41 and plunger sleeve 43 form a cylindrical cavity 43a for plunger 40 to descend within to a slit 12 (not shown) in administration port valve 44.

Compression member 42 serves to control the descent of plunger 40 in the cylindrical cavity 43a of administration port 10, and also serves to return plunger 40 to its normal position when the syringe fitting 21 is removed. Compression member 42 also prevents a luer tip from locking into valve cap 41 because compression member 42, e.g., a spring, forces plunger 40 back to the normal position, thereby ejecting the luer tip. Thus, compression member 42 keeps plunger 40 in normal position unless threaded sector 21a and complementary threaded sector 21b are engaged with one another via rotational movement of syringe fitting 21 having threaded sector 21a.

Washer 45 may be included to assist in providing a tight seal of the components to base 46. Preferably, body portion 26, valve cap 41, and plunger sleeve 43 are manufactured from medical grade polycarbonate. Fluid controller 22 handle is preferably manufactured from medical grade high density polyethylene. Administration port valve 44 is preferably manufactured from silicone 50 durometer shore A material. Other suitable materials can be used for the components disclosed herein.

Figure 2A:
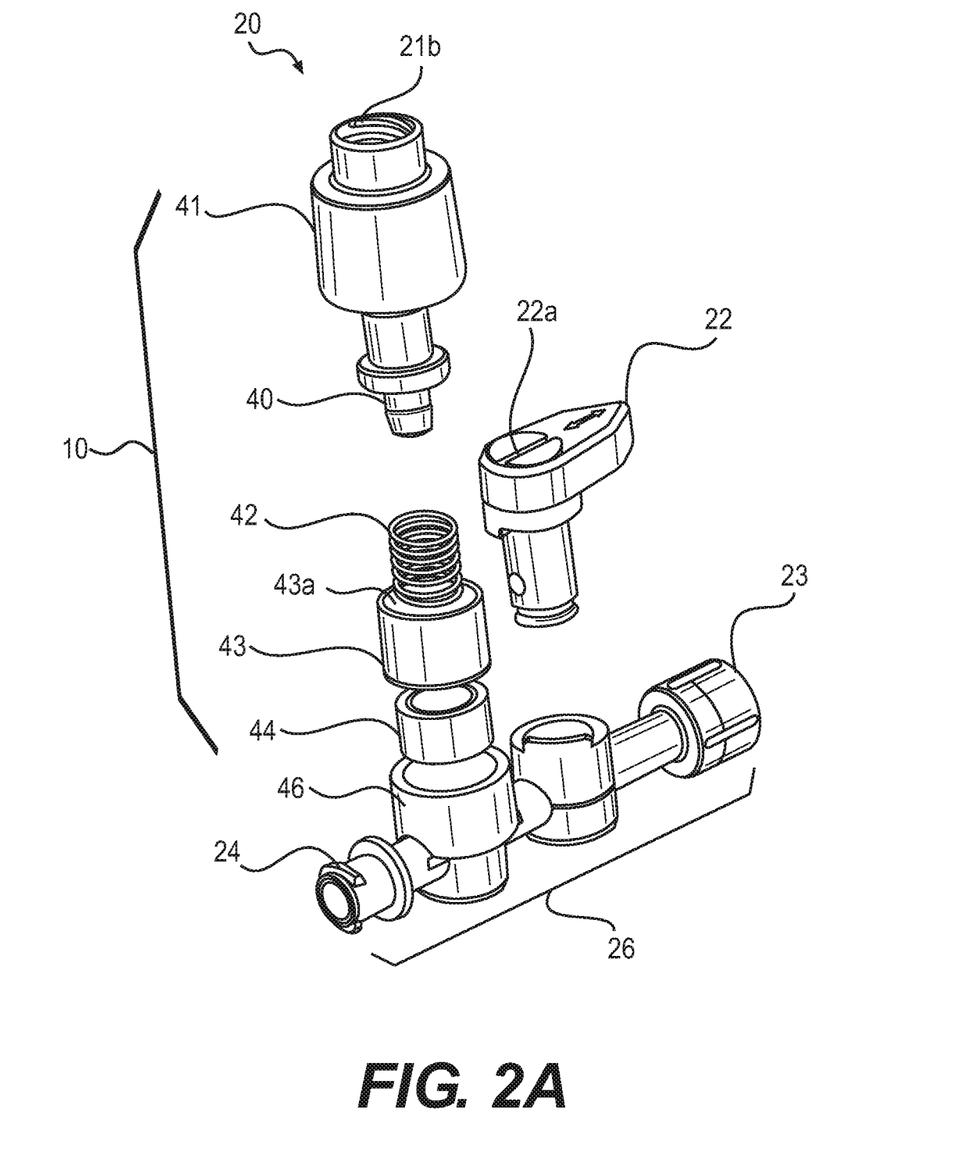
FIG. 2A shows a component view of another exemplary medical connector consistent with the present disclosure.
Figure 2B:
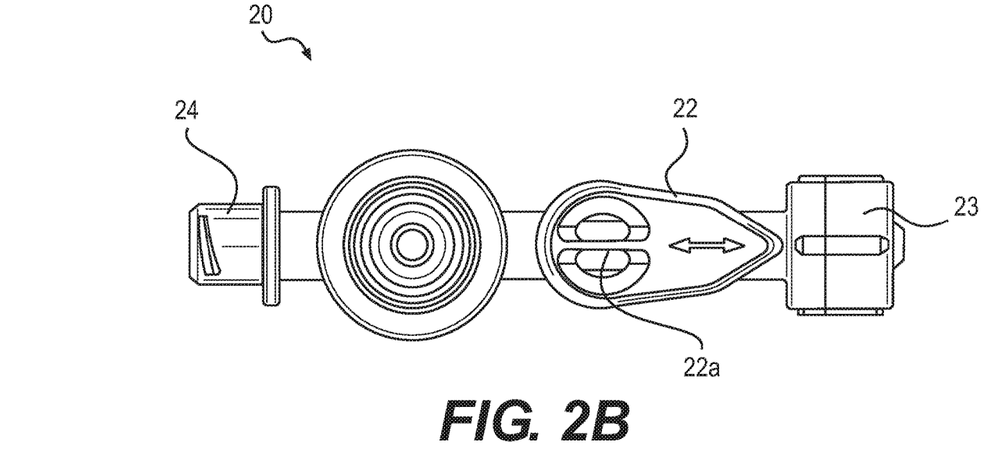
FIG. 2B shows a top view of the exemplary medical connector of FIG. 2A consistent with the present disclosure.
Figure 2C:
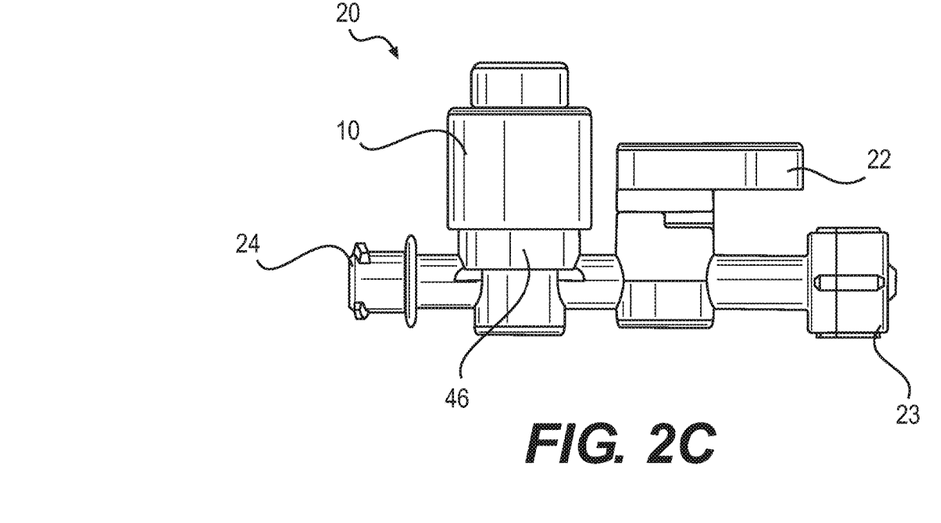
FIG. 2C shows a side view of the exemplary medical connector of FIG. 2A consistent with the present disclosure.

In FIGS. 1A and 1B, proximal fluid delivery device fitting 23 is shown as a barbed fitting, but may be any suitable form. In some embodiments, proximal fluid delivery device fitting 23 is preferably a non-luer compatible form in compliance with AAMI/CN3:2014 and ISO/ANSI 80369-3. For example, FIG. 2A shows a component view of another exemplary medical connector 20, FIG. 2B shows a top view of the exemplary medical connector 20 of FIG. 2A, and FIG. 2C shows a side view of the exemplary medical connector 20 of FIG. 2A. In the embodiment shown in FIGS. 2A-2C, proximal fluid delivery device fitting 23 is a male fitting in compliance with AAMI/CN3:2014 and ISO/ANSI 80369-3, such as an ENFit male connector. Additionally or alternatively, as shown in FIGS. 1A, 1B, and 2A-2C, distal patient access fitting 24 may be a screw-thread type female fitting in compliance with AAMI/CN3:2014 and ISO/ANSI 80369-3, such as an ENFit female connector, but may optionally take other suitable forms. In some embodiments, adaptors may be used on distal patient access fitting 24 and/or on proximal fluid delivery device fitting 23 to accommodate connection with other fitting forms. One such adaptor is commonly referred to as CEDIC® transition adaptor, and serves to convert an AAMI/CN3:2014 and ISO/ANSI 80369-3 screw-thread type fitting into a stepped form fitting.

In some embodiments, as shown in FIGS. 2A and 2B, the handle of fluid controller 22 may have a top surface that is embossed or debossed with a single-direction or double-direction arrow. Additionally or alternatively, the top surface may include a recessed area having a bar 22a crossing through. The bar may be molded in the recessed area. In other embodiments, the top surface and/or the recessed area of the top surface may be substantially flat. Bar 22a of the recessed area or the flat surface prevents mistaken connection of syringe fitting 21 to fluid controller 22.

Figure 3A:
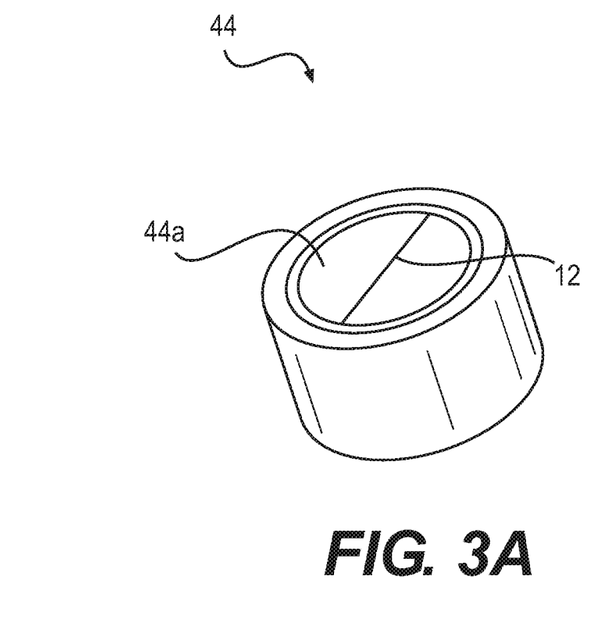
FIG. 3A shows a perspective view of an exemplary administration port valve, which may be used in connection with the exemplary medical connector of FIGS. 1A-2C consistent with the present disclosure.
Figure 3B:
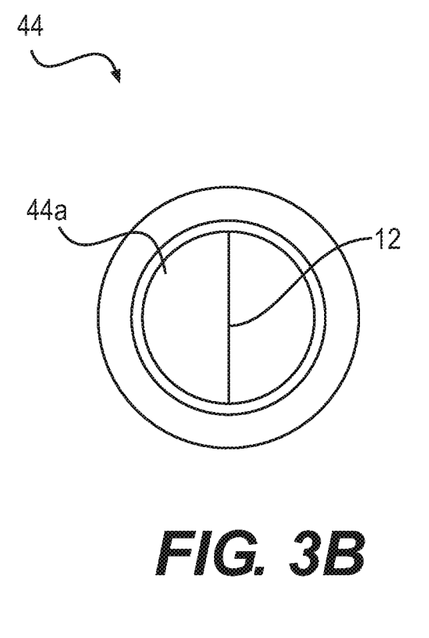
FIG. 3B shows a top view of the exemplary administration port valve of FIG. 3A consistent with the present disclosure.

FIG. 3A shows a perspective view of an exemplary administration port valve 44 and FIG. 3B shows a top view of administration port valve 44. As shown inn FIGS. 3A and 3B, administration port valve 44 described herein may include an administration port seal 44a about 0.075 inches thick, with slit 12 piercing administration port seal 44a. In this exemplary embodiment, slit 12 is approximately 0.325 inches long. Administration port seal 44a may be made in accordance with aspects of the disclosure of U.S. Pat. No.

8,353,895. Administration port seal 44a is normally closed and withstands backpressure to prevent leakage.

Figure 4A:
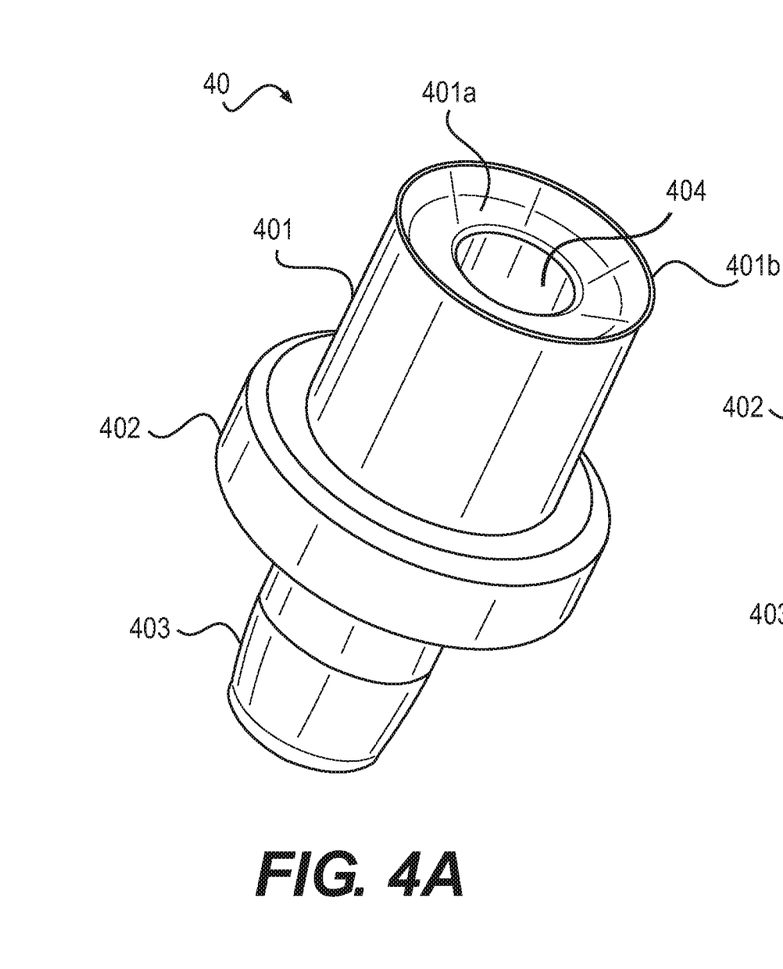
FIG. 4A shows a perspective view of an exemplary plunger, which may be used in connection with the exemplary medical connector of FIGS. 1A-2C consistent with the present disclosure.
Figure 4B:
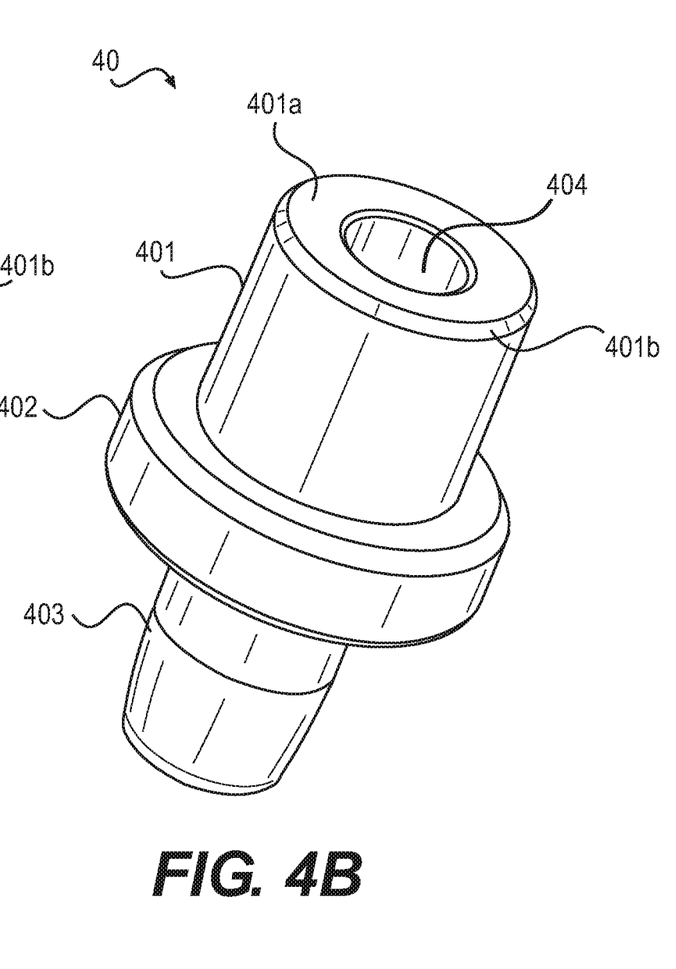
FIG. 4B shows a perspective view of another exemplary plunger, which may be used in connection with the exemplary medical connector of FIGS. 1A-2C consistent with the present disclosure.

FIG. 4A shows a perspective view of an exemplary embodiment of plunger 40, and FIG. 4B shows a perspective view of another exemplary embodiment of plunger 40. As shown in FIGS. 4A and 4B, plunger 40 may include a top portion 401, an external ring or collar 402, and below ring 402, a bottom portion 403, which may be molded or fused together, or manufactured as a single component. Ring 402 extends radially from a cylindrical cavity 404 portion of plunger 40. Bottom portion 403 may be a tapered portion. When plunger 40 is actuated, bottom portion 403 pierces slit 12 of administration port seal 44a. The cylindrical cavity portion of plunger 40 is preferably 2.9 mm in diameter, which further prevents misconnection with a luer tipped I.V. catheter or oral tip syringe. Ring 402 may be continuous and cylindrical, or it may optionally be comprised of wings or other such protrusions sufficient to actuate compression member 42 in the presence of a downward force onto plunger 40.

The configuration of plunger 40 allows the dimensional requirement of AAMI/CN3:2014 and ISO/ANSI 80369-3 to be met, because the diameter of top portion 401 allows plunger 40 to be depressed when rotational movement of the similarly-sized syringe fitting 21 occurs. For example, in the fully-engaged position of syringe fitting 21 into administration port 10, the cylindrical tip of syringe fitting 21 physically contacts and provides a downward force onto the cylindrical top portion 401 of plunger 40, thereby providing compression force to compression member 42 via ring 402.

Plunger 40 may be made with any suitable medical grade material. For example, plunger 40 may be made with a soft material, such as santoprene, or a hard material, such as high-density polyethylene (HDPE) or high-density polypropylene (HDPP), or a combination of a soft material and a hard material. The combined material may be formed by over molding two materials or from a blended formulation of two materials. For example, santoprene may be over molded on top of HDPE or HDPP. Alternatively, raw santoprene may be blended with raw polypropylene to form a blended formulation, which is then formed into the material of plunger 40. The proportion of santoprene in the blended formulation may range from about 5% to about 15%.

In some embodiments, top portion 401, ring 402, and/or bottom portion 403, may be made of the same material, such as a soft material, a hard material, or a combination of a soft material and a hard material. In other embodiments, plunger 40 may be made of a non-uniform composition. For example, the materials of top portion 401, ring 402, and/or bottom portion 403, may be made of different materials. For example, the material of top portion 401 may be different from the material of bottom portion 403. Top portion 401 is preferably made of a soft material, which may increase the sealing of plunger 40 with syringe fitting 21 by increasing the friction between the contacting surfaces. This configuration may further prevent plunger 40 engaged with syringe fitting 21 from being pushed back by compression member 42 before a user applies an opposite rotational movement to purposefully disengage the plunger. Bottom portion 403 may be preferably made of a hard material to pierce slit 12 of administration port seal 44a. The material of ring 402 may be the same as that of top portion 401 or that of bottom portion 403. In some embodiments, top portion 401 may include a top part and a bottom part attached to ring 402. In such instances, the top part of top portion 401 may be made of a soft material, whereas the bottom part may be made of a hard material as that of ring 402 and/or bottom portion 403.

As shown in FIG. 4A, top portion 401 may have an end surface 401a and an edge 401b. In some embodiments, end surface 401a is sloped, which may facilitate the engagement of syringe fitting 21 with plunger 40 and thus the activation of plunger 40. In other embodiments, as shown in FIG. 4B, end surface 401a is flat. Additionally or alternatively, as shown in FIG. 4A, edge 401b of top portion 401 may have a right angle, be leveled, or chamfered. In other embodiments, as shown in FIG. 4B, edge 401b of top portion 401 may be sloped and have an angle smaller than a right angle, forming a chamfer on top portion 401. The angled, leveled, or chamfered edge 401b may facilitate plunger 40 to return to its normal position when syringe fitting 21 is purposefully removed by reducing the friction between edge 401b and syringe fitting 21.

Figure 4C:
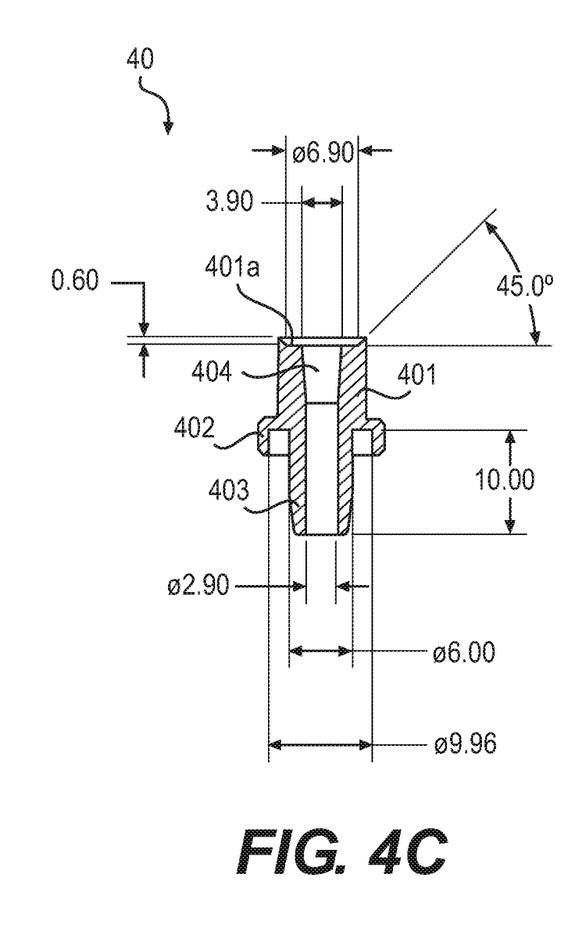
FIG. 4C shows a cross-sectional view of another exemplary plunger, which may be used in connection with the exemplary medical connector of FIGS. 1A-2C consistent with the present disclosure.
Figure 4D:
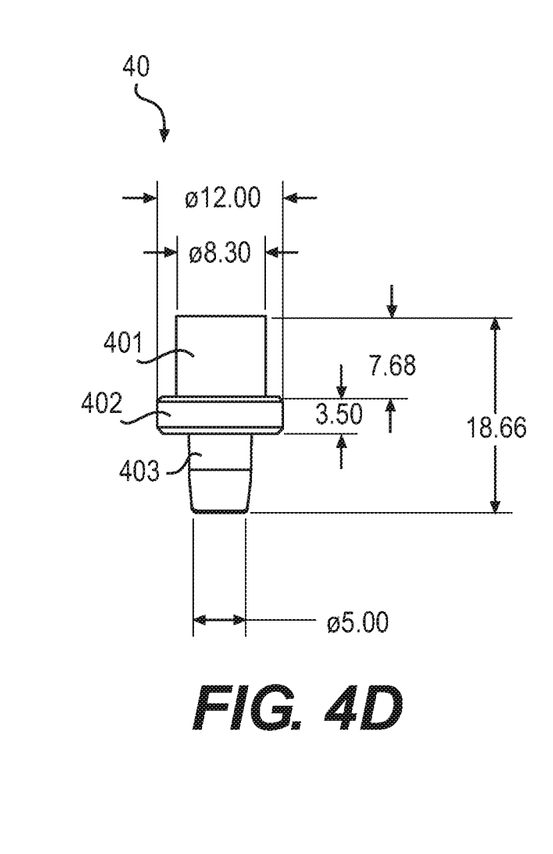
FIG. 4D shows a front view of another exemplary plunger, which may be used in connection with the exemplary medical connector of FIGS. 1A-2C consistent with the present disclosure

In one exemplary embodiment, as shown in FIGS. 4C and 4D, plunger 40 may have a height nominally of 18.66 mm along its longitudinal axis, which extends from end surface 401a of top portion 401 to the end of bottom portion 403. Top portion 401 may have a height nominally of 7.68 mm along the longitudinal axis of plunger 40, and ring 402 may have a height nominally of 3.5 mm along the longitudinal axis of plunger 40. Top portion 401 may have an outer diameter nominally of 8.3 mm. Ring 402 may have an external diameter nominally of 12 mm and an internal diameter nominally of 9.96 mm. The cylindrical cavity of plunger 40 may have an elongated tapered shape extending throughout the inside of plunger 40 along the longitudinal axis of plunger 40. The cylindrical cavity may have an internal diameter nominally of 2.9 mm at the end of bottom portion 403 and an internal diameter nominally of 3.9 mm at end surface 401a of top portion 401. End surface 401a of top portion 401 may have an outer diameter nominally of 6.9 mm and/or a height nominally of 0.6 mm along the longitudinal axis of plunger 40.

Using medical connector 20 for enteral applications is further described below with reference to FIGS. 5A and 5B. FIG. 5A shows a cross-sectional view of medical connector 20 with an exemplary syringe having syringe fitting 21 ready to actuate plunger 40. FIG. 5B shows another cross-sectional view of medical connector 20 with the syringe actuating plunger 40, causing administration port slit 12 to open.

As shown in FIG. 5A, plunger 40 is in its normal position, syringe fitting 21 is ready to actuate plunger 40, and slit 12 of administration port seal 44a is closed. Syringe fitting 21 may be manually or automatically operated to engage with administration port 10 using a rotational movement to actuate plunger 40, causing syringe fitting 21 to open slit 12 and becoming in fluid connection with body portion 26 of medical connector 20. As shown in FIG. 5B, syringe fitting 21 is at least partially or fully actuating plunger 40, causing slit 12 of administration port seal 44a to open, permitting fluid communication between the fluid flow paths of the syringe and body portion 26 of medical connector 20.

As described herein, syringe fitting 21 may be a female tip, which may be a syringe tip in compliance with AAMI/CN3:2014 and ISO/ANSI 80369-3. Syringe fitting 21 actuates plunger 40 via compression member 42. The rotational movement of threaded sector 21a of syringe fitting 21 traverses complementary threaded sector 21b of administration port 10 (shown in FIG. 1B), causing syringe fitting 21 to descend into valve cap 41 (shown in FIG. 1B), pushing down on plunger 40, which penetrates through slit 12. This movement in turn depresses compression member 42.

During the rotational movement of syringe fitting 21, plunger 40 descends such that it pierces administration port seal 44a, opening slit 12 and permitting fluid communication from syringe fitting 21 of the syringe into body portion 26, or vice versa. A reversed-direction rotational movement of syringe fitting 21 causes compression member 42 to decompress, forcing plunger 40 back into its normal position, thereby closing slit 12 of administration port seal 44a. When plunger 40 is in its normal position and slit 12 is closed, fluid communication through administration port 10 from syringe fitting 21 to body portion 26 or vice versa is prevented.

As described herein, compression member 42 is preferably a coil spring made of polymer material or MR-conditional or MR-safe metal. Compression member 42 may be, in some embodiments, a coil spring manufactured from stainless steel 316 grade carbon fiber alloy, or other suitable material. Other configurations for compression member 42 include, but are not limited to, open or closed cell foam (e.g., Neoprene, EPDM, Polyurethane, etc.); solid elastomeric compounds (e.g., Buna, EPDM, Silicone, Viton, etc.); compressed air-pneumatic; compressed liquid-hydraulic; standing bristle fibers that bend when they are compressed (e.g., Nylon); disc springs (e.g., Wave washers, Belleville, etc.); or elastomer stretch springs, which operate like mini rubber bands that stretch down and then retract the plunger; or protrusions from the plunger component made from plastics or other suitable material.

Figure 6:
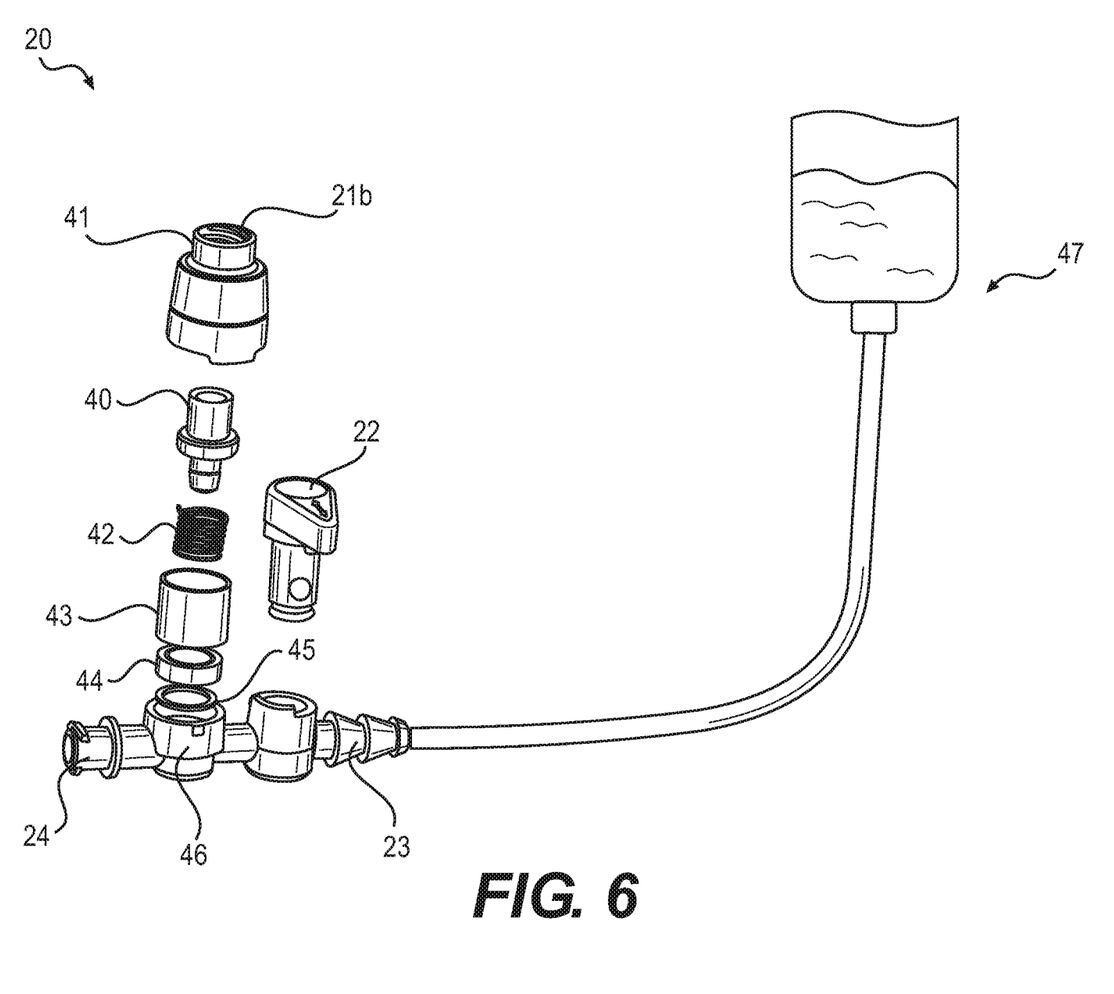
FIG. 6 shows an optional configuration for the exemplary medical connector of FIGS. 1A-2C with an exemplary enteral feeding administration set attached.

FIG. 6 shows an optional configuration for using medical connector 20 with an exemplary enteral feeding administration set 47. Enteral feeding administration set 47 is permanently attached to body portion 26 of medical connector 20 via proximal fluid delivery device fitting 23. In this optional configuration, proximal fluid delivery device fitting 23 could be any type of fitting and would not necessarily need to be in compliance with AAMI/CN3:2014 and ISO/ANSI 80369-3 or other applicable standards, being a permanent connection. In further alternate embodiments, only the tubing portion of enteral feeding administration set 47 could be permanently attached to body portion 26.

As can be seen, the design, development, and creation of the present disclosure provides for a unique closed triple-ported connector system with non-luer compatible access ports designed and configured for maximum patient safety for present day use as well as anticipation for meeting any future universal enteral feeding device connections as envisioned by the proposed AAMI/CN3:2014 and ISO/ANSI 80369-3 standards.

Other embodiments will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. A three port medical connector for enteral applications, the medical connector comprising:
    a body portion having
        a first port including a distal patient access fitting,
        a second port including a proximal fluid delivery device fitting,
        a fluid flow path formed between the first and second ports,
        a fluid flow controller disposed between the first and second ports for controlling a flow of fluid within the fluid flow path; and
        a third administration port used to administer or withdraw fluids from the fluid flow path and to prevent connection of the third administration port to a luer-type syringe, the third administration port comprising:
            a first cylindrical cavity including internally facing threads dimensioned to receive externally facing threads of an ISO/ANSI 80369-3 compliant non-luer female connector,
            an administration port seal having a single normally-closed slit located substantially in a center of the seal for accessing the fluid flow path, wherein opening the single slit creates an open fluid flow path through the administration port seal,
            a plunger comprising a second cylindrical cavity and an external ring disposed outside the second cylindrical cavity,
            and
        a spring received in the external ring of the plunger that biases the plunger away from the single slit, wherein when said externally threaded non-luer female connector screws into said first cylindrical cavity and engages said internally facing threads the non-luer female connector causes the plunger to compress the spring and move towards the single slit such that an end of the plunger opens the single normally-closed slit wherein the external ring is disposed about the spring such that a downward force on the external ring actuates the spring.

2. The medical connector of claim 1, wherein the plunger is made of a non-uniform composition.

3. The medical connector of claim 2, wherein the plunger comprises a top portion and a bottom portion, wherein the top portion is made of a material softer than the bottom portion.

4. The medical connector of claim 3, wherein the top portion is made of santoprene.

5. The medical connector of claim 3, wherein the bottom portion is made of high-density polyethylene (HDPE) or high-density polypropylene (HDPP).

6. The medical connector of claim 3, wherein the top portion comprises a chamfered edge.

7. The medical connector of claim 3, wherein the ring is made of the same material as the top portion.

8. The medical connector of claim 3, wherein the top portion, the ring, and/or the bottom portion is made of a blended formulation comprising high-density polyethylene (HDPE) or high-density polypropylene (HDPP) and santoprene, wherein a proportion of the HDPE or HDPP ranges from about 5-15%.

9. The medical connector of claim 1, wherein the second cylindrical cavity has an elongated tapered shape extending throughout an inside of the plunger and has an internal diameter nominally of 2.9 mm at a first end and an internal diameter nominally of 3.9 mm at a second end.

10. The medical connector of claim 1, wherein the first cylindrical cavity comprises a complementary threaded sector to the ISO/ANSI 80369-3 compliant non-luer female connector, and
    wherein the ISO/ANSI 80369-3 compliant non-luer female connector engages with the third administration port using a rotational movement, causing an at least one threaded sector of the ISO/ANSI 80369-3 compliant non-luer female connector to traverse the complementary threaded sector.

11. The medical connector of claim 10, wherein the cylindrical cavity has dimensions in compliance with dimensions set forth in AAMI/CN3:2014 and ISO/ANSI 80369-3.

12. The medical connector of claim 11, wherein the ISO/ANSI 80369-3 compliant non-luer female connector has dimensions in compliance with AAMI/CN3:2014.

13. The medical connector of claim 1, wherein the distal patient access fitting has a fluid flow path having an internal diameter nominally of 2.9 mm.

14. The medical connector of claim 1, wherein the proximal fluid delivery device fitting has a fluid flow path having an internal diameter nominally of 2.9 mm.

15. The medical connector of claim 1, wherein a fluid flow path of the distal patient access fitting and a fluid flow path of the proximal fluid delivery device fitting have diameters nominally of 2.9 mm.

16. The medical connector of claim 1, wherein the fluid flow controller is disposed between the administration port seal and the proximal fluid delivery device fitting.

17. The medical connector of claim 16, wherein the fluid flow controller is a manually operated turn handle that has fixed stop positions for both an on and off fluid flow positions.

18. The medical connector of claim 17, wherein when the turn handle is at the on fluid flow position, the distal patient access fitting, the proximal fluid delivery device fitting, and the administration port are all in fluid communication with the fluid flow path positioned within the body portion.

19. The medical connector of claim 1, wherein the proximal fluid delivery device fitting is permanently attached to an enteral feeding administration set.

* * * * *